(12) United States Patent
Waldmann et al.

(10) Patent No.: US 8,758,519 B2
(45) Date of Patent: Jun. 24, 2014

(54) METHOD FOR TESTING THE PATENCY OF AN ENDOSCOPIC CHANNEL AND AN ENDOSCOPE WASHING MACHINE FOR SAME

(75) Inventors: Jens Waldmann, Hamburg (DE); Sascha Eschborn, Ahrensburg (DE)

(73) Assignee: Olympus Winter & Ibe GmbH, Hamburg (DE)

( * ) Notice: Subject to any disclaimer, the term of this patent is extended or adjusted under 35 U.S.C. 154(b) by 536 days.

(21) Appl. No.: 12/996,231

(22) PCT Filed: May 28, 2009

(86) PCT No.: PCT/EP2009/003819
§ 371 (c)(1),
(2), (4) Date: Feb. 16, 2011

(87) PCT Pub. No.: WO2009/146839
PCT Pub. Date: Dec. 10, 2009

(65) Prior Publication Data
US 2011/0126868 A1    Jun. 2, 2011

(30) Foreign Application Priority Data
Jun. 3, 2008    (DE) .......................... 10 2008 026 445

(51) Int. Cl.
*A61B 1/12*    (2006.01)
(52) U.S. Cl.
USPC .................. 134/22.12; 134/22.1; 134/166 C; 422/28; 422/105

(58) Field of Classification Search
CPC ........................................................ A61B 1/121
USPC ...................................................... 134/22.12
See application file for complete search history.

(56) References Cited

U.S. PATENT DOCUMENTS

| 5,279,799 A | 1/1994 | Moser |
| 2007/0100203 A1 | 5/2007 | Jackson et al. |
| 2007/0100204 A1 | 5/2007 | Feld et al. |

FOREIGN PATENT DOCUMENTS

| EP | 0 709 056 A1 | 5/1996 | |
| EP | 0 711 529 A1 | 5/1996 | |
| EP | 1 779 769 A2 | 5/2007 | |
| JP | 06319698 A * | 11/1994 | ............... A61B 1/12 |

OTHER PUBLICATIONS

English machine translation of JP06319698A.*
International Search Report dated Sep. 1, 2009.
German Examination Report dated Apr. 27, 2009.

* cited by examiner

*Primary Examiner* — Michael Barr
*Assistant Examiner* — Jason Riggleman
(74) *Attorney, Agent, or Firm* — Scully, Scott, Murphy & Presser, P.C.

(57) ABSTRACT

A method for testing the patency of an endoscopic channel in an endoscope washing machine. In the method, the entrance of the channel is pressurized and then blocked, whereupon the pressure change at the entrance is measured. Where the channel is pressurized using a sequence of pressure pulses, and the maximum and minimum values thereof are determined.

2 Claims, 1 Drawing Sheet

METHOD FOR TESTING THE PATENCY OF AN ENDOSCOPIC CHANNEL AND AN ENDOSCOPE WASHING MACHINE FOR SAME

CROSS-REFERENCE TO RELATED APPLICATION

The present application is based upon and claims the benefit of priority from the PCT/EP2009/003819 filed on May 28, 2009, the entire contents of which are incorporated herein by reference.

BACKGROUND

1. Field

The present invention relates to an endoscope washing, and particularly to method for testing the patency of an endoscopic channel and endoscope washing machine for same.

2. Description of the Related Art

Endoscopes, in particular flexible endoscopes, have long, narrow channels, which are used to conduct, for example, liquid or gas. When machining washing and disinfecting an endoscope in an endoscope washing machines, the channels must also be rinsed through. In order to guarantee a good cleaning and disinfection result, it is necessary to check the endoscope channels beforehand for patency. Endoscope washing machines are equipped with appropriate devices.

A generic endoscope washing machine is known from EP 0 709 056 A1. In this case, in order to test patency, the endoscopic channel to be tested is pressurized and then blocked and the subsequent pressure loss is recorded. Extremely accurate pressure gauges as well as a costly measuring process are needed for this and it is difficult to distinguish between different stages of patency.

The problem of the present invention consists in creating a patency test, which will provide clear results simply.

SUMMARY

According to the invention the channel being tested is pressurized using a sequence of pressure pulses. A switching valve controlled by a sequence of pulses can generate this sequence simply. The pressure is measured between the valve and the entrance to the channel. The measured pressure pulses are obtained, which differ in a characteristic way, depending on the patency of the channel. If the channel is normally patent, then the pulses are mainly obtained with the full pressure stroke between 0 and pump pressure. If the channel is blocked, the same pulses are obtained but with a much reduced pulse amplitude—to be precise, at absolutely raised pressure level at the range of the pump pressure. If the channel is not connected at all (a vital test point), then, with a small stroke at low absolute pressure level, the pulses are in the range of 0. These three different results can be very easily and clearly distinguished and, using simple means, very quickly result in a clear statement about the patency of the channel.

Advantageously, according to claim 2, only two values are measured, namely the relative amplitude of the pulses and their absolute height. Measurement is therefore simplified to what is essential.

An endoscope washing machine to perform the method according to the invention is indicated in claim 3. A preferred embodiment is indicated in claim 4. The ability of the elastic connecting line to increase its volume ensures certain pressure storage when the switching valve is closed, so that if the channel is blocked, the pressure remains high, even when the valve is closed.

BRIEF DESCRIPTION OF THE DRAWINGS

In the drawing, the invention is described diagrammatically and by way of examples.

DETAILED DESCRIPTION

Figure 1:
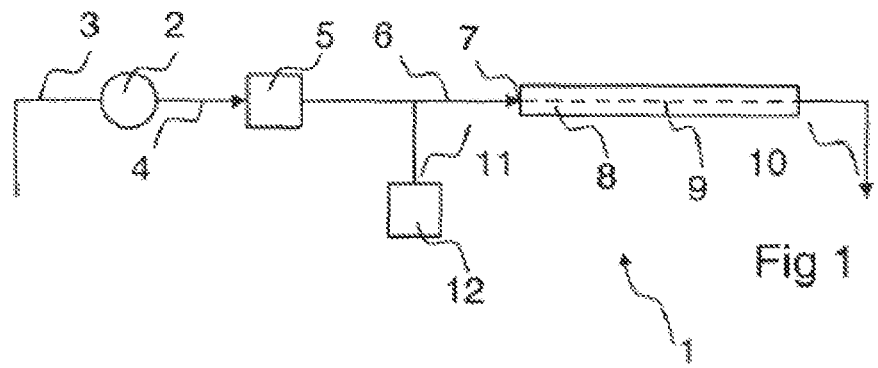
FIG. 1 shows a block diagram of a device for testing for patency.

FIG. 1 shows part of an endoscope washing machine, not presented in greater detail, namely a device 1 for testing patency. This comprises a pump 2, which sucks up washing liquid with a suction line 3 and conveys it via a pressure line 4 to a switching valve 5, which is controlled in such a way that it opens and closes in a sequence of pulses. A connecting line 6 leads from the switching valve 5 to the entrance 7 of a channel 9, represented by a dotted line and located in an endoscope 8. The liquid drains from the outlet of the channel 9 via a discharge line 10.

A pressure gauge 12 is connected to the connecting line 6 via a second line 11.

Figure 2:
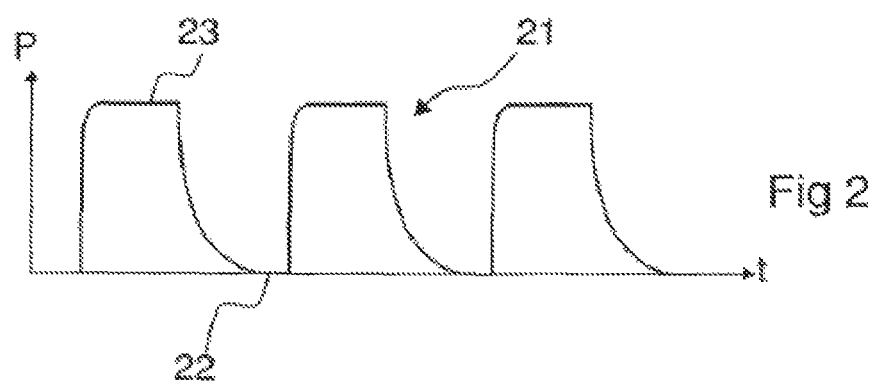
FIGS. 2 to 4 show pulse diagrams for different test results.
Figure 3:
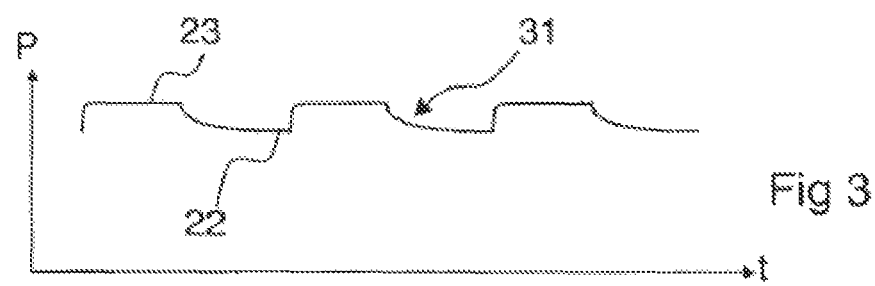
Figure 4:
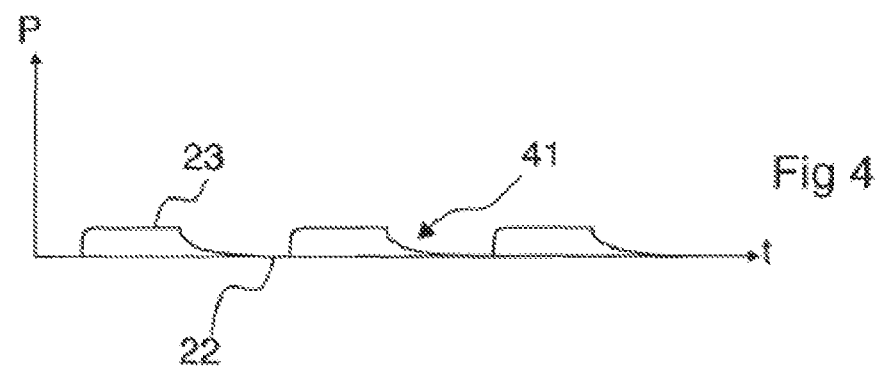

The switching valve is opened and closed by a sequence of pulses and thereby generates pulses in the connecting line 6, as shown in FIGS. 2-4 in each case with the pressure P plotted against the time t.

FIG. 2 shows the sequence of pulses 21 of the pressure pulses measured by the pressure gauge 12 in the connecting line 6 for a normally patent channel 9. If the switching valve 5 is open, the pressure rises to the maximum value 23 corresponding to the pump pressure and falls if the valve is closed to the minimum value 22, i.e. essentially to 0, because the liquid can rapidly flow away through the channel 9. This result is therefore characterised by the large pulse stroke.

FIG. 3 shows the sequence of pulses 31 measured in the case of a blocked channel 9. If the switching valve 5 is closed, the liquid cannot drain away through the blocked channel 9 or only in very small amounts. The pressure remains at a high level even during the pulse intervals, i.e. at the minimum values 22, as shown by FIG. 3. Pulses with a low stroke are measured at a high absolute pressure level.

FIG. 4 shows the measured sequence of pulses 41 where the connecting line 6 is not properly connected to the entrance 7 of the channel 9. Liquid can escape from the connecting line 6 without any counter-pressure. Only a very low pressure can build up in this connecting line, if the switching valve 5 opens. In other words, the result, as FIG. 4 shows, is pulses with low stroke at a low pressure level.

The results according to FIGS. 2-4 can be distinguished at first glance even by untrained staff and by simple machines, without risk of confusion. In other words, using a very simple machine and in a short measuring time, the essential patency situations can be distinguished, which can occur in an endoscope channel, namely a normally patent and correctly connected channel with the result shown in FIG. 2, a blocked channel with the result shown in FIG. 3 and the channel not connected with the result shown in FIG. 4.

The frequency of the pulses used in the device 1 shown to control the switching 5, can be in the order of 1 Hz.

As FIGS. 2-4 show, the resulting pressure pulses in the edge areas are somewhat rounded, but this does not upset the results in any way, where it is merely a matter of determining the characteristic differences between FIGS. 2 to 4. For this the precise shape of the pressure pulse plays no part. Only the respective maximum values 23 and minimum values 22 have to be determined.

The connecting line 6 should possess a certain amount of volume flexibility. It can, for example, be developed as an elastic hose line or can be connected to an elastic expansion vessel or the like. This guarantees certain pressure storage which, when the switching valve 5 is closed, enables the pressure according to FIG. 3 to be kept high.

The invention claimed is:

1. A method for testing the patency of an endoscopic channel in an endoscope washing machine, the method comprising:
    pressurizing an entrance of the channel being pressurized using a sequence of at least two pressure pulses, wherein a frequency of pressure pulses is about 1 Hz;
    blocking the entrance of the channel being pressurized;
    measuring the pressure change at the entrance; and
    determining the patency of the channel based on maximum and minimum values of the measured pressure change.

2. The method according to claim 1, furthering comprising measuring a relative amplitude of the pressure pulses and their absolute height.

* * * * *